(12) United States Patent
Yamagishi et al.

(10) Patent No.: US 7,220,808 B2
(45) Date of Patent: May 22, 2007

(54) THIOL COMPOUND, COPOLYMER AND METHOD FOR PRODUCING THE COPOLYMER

(75) Inventors: Takanori Yamagishi, Funabashi (JP); Takahito Mita, Ichihara (JP)

(73) Assignee: Maruzen Petrochemical Co. Ltd., Tokyo (JP)

( * ) Notice: Subject to any disclaimer, the term of this patent is extended or adjusted under 35 U.S.C. 154(b) by 262 days.

(21) Appl. No.: 10/784,435

(22) Filed: Feb. 23, 2004

(65) Prior Publication Data

US 2004/0181023 A1    Sep. 16, 2004

(30) Foreign Application Priority Data

Mar. 10, 2003    (JP)    ............................. 2003-063850

(51) Int. Cl.
*C08F 2/38*    (2006.01)
(52) U.S. Cl. ..................... 526/212; 526/224; 526/280
(58) Field of Classification Search .............. 526/212, 526/224, 280
See application file for complete search history.

(56) References Cited

U.S. PATENT DOCUMENTS 6,653,419 B1 * 11/2003 Petrov et al. ............... 526/247

FOREIGN PATENT DOCUMENTS

| JP | 59-45439 | 3/1984 |
|---|---|---|
| JP | 62-115440 | 5/1987 |
| JP | 3-223860 | 10/1991 |
| JP | 4-104251 | 4/1992 |
| JP | 4-219757 | 8/1992 |
| JP | 5-113667 | 5/1993 |
| JP | 7-209868 | 8/1995 |
| JP | 9-73173 | 3/1997 |
| JP | 10-55069 | 2/1998 |
| JP | 10-239846 | 9/1998 |
| JP | 11-65120 | 3/1999 |
| JP | 2000-19737 | 1/2000 |
| JP | 2001-117231 | 4/2001 |
| JP | 2002-20424 | 1/2002 |

* cited by examiner

*Primary Examiner*—Helen L. Pezzuto
(74) *Attorney, Agent, or Firm*—Melvin I. Stoltz

(57) ABSTRACT

By resolving objections in the prior art, provided are a novel copolymer suitable as a coating polymers which is excellent in adhesion to a substrate and can be used suitably as the polymer for the coating film having durability against pattern collapse in the finer pattern formation for progressed lithography technology and a method for producing the copolymer, as well as a novel thiol compound useful as a chain transfer agent in the production of the copolymer. The novel thiol compound of the present invention has the structure represented by the formula (1);

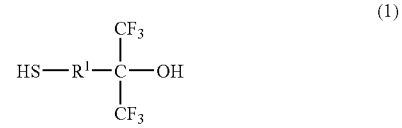

(1)

wherein $R^1$ is a bivalent substituent selected from linear, branched or cyclic saturated hydrocarbon having 1 to 15 carbon atoms.

5 Claims, No Drawings

THIOL COMPOUND, COPOLYMER AND METHOD FOR PRODUCING THE COPOLYMER

BACKGROUND OF THE INVENTION

1. Field of the Invention

The present invention relates to a novel thiol compound useful as a chain transfer agent, a copolymer in radical copolymerization using the thiol compound as the chain transfer agent, and methods for producing the same. More particularly, the present invention relates to the copolymer suitably used for coating film in lithography such as resist film and anti-reflective coating, and the method for producing the same, as well as the novel thiol compound useful as the chain transfer agent in the production of the copolymer.

2. Description of Related Art

In semiconductor lithography, the formation of finer patterns has been required in conjunction with increase of integration degree. It is essential for micropatterning techniques to make a wavelength of irradiation light source shorter. Currently, the lithography by krypton fluoride (KrF) excimer laser (wavelength 248 nm) has become a mainstream, and the micropatterning techniques of 100 nm linewidth or less by argon fluoride (ArF) excimer laser (wavelength 193 nm) is coming into practical use. The micropatterning techniques using fluorine dimer ($F_2$) excimer laser (wavelength 157 nm), extreme-ultraviolet ray (EUV), X-ray, electron beam, and the like are in developmental stages.

The resist polymer used for these lithography technologies has essentially a repeating unit having a non-polar substitute which is decomposed by an acid and becomes soluble in an alkali developer and a repeating unit having a polar group to enhance adhesion to a substrate. And if necessary, the resist polymer is comprising a repeating unit having non-polar substitutes to regulate solubility in a resist solvent or the alkali developer. As these repeating units, for example, in the KrF lithography, hydroxystyrenes and derivatives thereof have been primarily used, and in the ArF lithography, (meth)acrylates and derivatives thereof and the like have been considered because the hydroxystyrenes absorb the light with a wavelength of 193 nm.

As specific examples of such resist polymers, copolymers of (meth)acrylic monomer with styrene type monomer (see e.g., Patent References 1 to 4), polymers containing hydroxystyrene which is partially protected with acetal (see e.g., Patent References 5 to 8) and the like are known in the KrF lithography, and copolymers of (meth)acrylic monomer having lactone structure (see e.g., Patent references 9 to 10) are known in the ArF lithography.

Whereas, even in the polymer comprising the repeating unit having the polar group to enhance the adhesion to the substrate as the above, it is a problem that finer patterns cannot be achieved because end-groups of the polymer derived from a initiator or a chain transfer agent used at the polymerization don't have sufficient adhesion property.

Also, in the resist pattern formation, it is a problem that resist patterns collapse due to surface tension of the washing water vaporizing in a drying process after development and rinsing. Especially, the pattern collapse occurs easily because a pattern-substrate contacting area becomes small when the pattern becomes finer. To avoid this, it is necessary to keep an aspect ratio (height/width) low, but on the other hand, it is required to make a coating film thick in order to satisfy dry etching resistance of the pattern, that is, to make the aspect ratio of the resist pattern high. Thus, the resist polymer with higher adhesion to the substrate where the aspect ratio can be increased and the pattern collapse does not occur even in fine pattern formation has been needed.

Thus, the several methods using a polymerization initiator and a chain transfer agent having a polar group have been studied to enhance adhesion of the resist polymer to the substrate. As an example using the polymerization initiator having a polar group, the method using the polymerization initiator having an oxygen-containing group or a substituted or unsubstituted amino group in the molecule is known (see e.g., Patent Reference 11). In the reference, hydroxyl group, carboxyl group, substituted oxyl group, substituted oxycarbonyl group, acyl group, substituted or unsubstituted carbamoyl group, hydroxyimino group, and substituted or unsubstituted oxyimino group are disclosed as the oxygen-containing groups. However, in the method of using carboxyl group, it has been a problem that swelling occurs easily in the alkali developing process after the exposure because of the strong hydrophilic property of carboxyl group, and then no stable pattern is obtained in finer lithography even if the alkali-solubility and the substrate adhesion can be improved. In the method of using hydroxyl group, substituted oxyl group, substituted oxycarbonyl group, acyl group and the like, it is insufficient to improve the adhesion to the substrate, because the polarity of these groups is weak. Furthermore, the method of using the oxygen-containing group comprising nitrogen atoms such as substituted or unsubstituted carbamoyl group, hydroxyimino group or substituted or un-substituted oxyimino group or the like, and the method of using the substituted or unsubstituted amino group are not practical, because these nitrogen-containing groups trap the acid generated from acid generator and make sensitivity lower.

At the same time, as examples using the chain transfer agent having the polar group, the method of using carboxyl group-containing thiol such as mercaptoacetic acid and mercaptopropionic acid as the chain transfer agent (see e.g., Patent Reference 12) and the method of using ester compounds thereof or hydroxyl group-containing thiol such as mercaptoethanol are known (see e.g., Patent Reference 13 to 14). However, also in these methods, as with the case of the above polymerization initiator, it is a problem that the swelling easily occurs at the alkali development in the method of using carboxyl group-containing thiol, and the adhesion to the substrate is insufficient in the method of using the ester compound or hydroxyl group-containing thiol, and both cannot reach to practical levels.

Moreover, in the lithography on a high reflective substrate, it is difficult to trace fine resist patterns due to halation of reflected lights. To solve this issue, an anti-reflective coating polymer is coated under a resist coating film and absorbs the reflected lights of the substrate. Furthermore, in the multi-layer resist application for progressed lithography technology, a bottom layer coating polymer is coated under the thin resist coating film and imaged by dry etching. For all these coating polymers, the adhesion to the substrate is important, and more excellent adhesion is required.

Patent Reference 1
    JP-A-59-45439
Patent Reference 2
    JP-A-5-113667
Patent Reference 3
    JP-A-7-209868
Patent Reference 4
    JP-A-11-65120
Patent Reference 5
    JP-A-62-115440

Patent Reference 6
  JP-A-4-219757
Patent Reference 7
  JP-A-3-223860
Patent Reference 8
  JP-A-4-104251
Patent Reference 9
  JP-A-9-73173
Patent Reference 10
  JP-A-10-239846
Patent Reference 11
  JP-A-2002-20424
Patent Reference 12
  JP-A-10-55069
Patent Reference 13
  JP-A-2000-19737
Patent Reference 14
  JP-A-2001-117231

SUMMARY OF THE INVENTION

The present invention has been completed against the above background, and the objective thereof is to provide a novel copolymer which has high adhesion and is suitable as polymer for coating film having durability against pattern collapse in the finer pattern formation and a method for producing the copolymer, as well as a novel thiol compound useful as a chain transfer agent in the production of the copolymers.

As a result of an intensive study to solve the problems above, the inventors of the present invention have found that adhesion to the substrate is remarkably improved in a copolymer obtained by using a novel thiol compound having a particular structure as a chain transfer agent, and have completed the present invention.

That is, the present invention provides a thiol compound having the structure represented by the following formula (1)

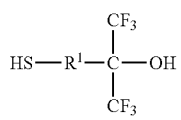
(1)

wherein $R^1$ is a bivalent substituent selected from linear, branched or cyclic saturated hydrocarbon having 1 to 15 carbon atoms, and a copolymer obtained by radical copolymerization of two or more polymerizable compounds having an ethylenic double bond using the thiol compound as a chain transfer agent.

Also, the present invention provides a method for producing the copolymer where the thiol compound represented by the above formula (1) is used as the chain transfer agent in the radical copolymerization of two or more polymerizable compounds having the ethylenic double bond.

DETAILED DESCRIPTION OF THE INVENTION

The present invention is described in more detail below.

In the thiol compound of the present invention, the substituent represented by $R^1$ in the formula (1) is not particularly limited as long as it is a bivalent substituent selected from linear, branched or cyclic saturated hydrocarbon having 1 to 15 carbon atoms, and specific examples of this $R^1$ can include the following structures.

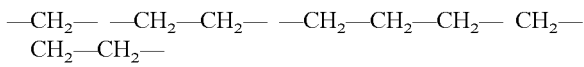

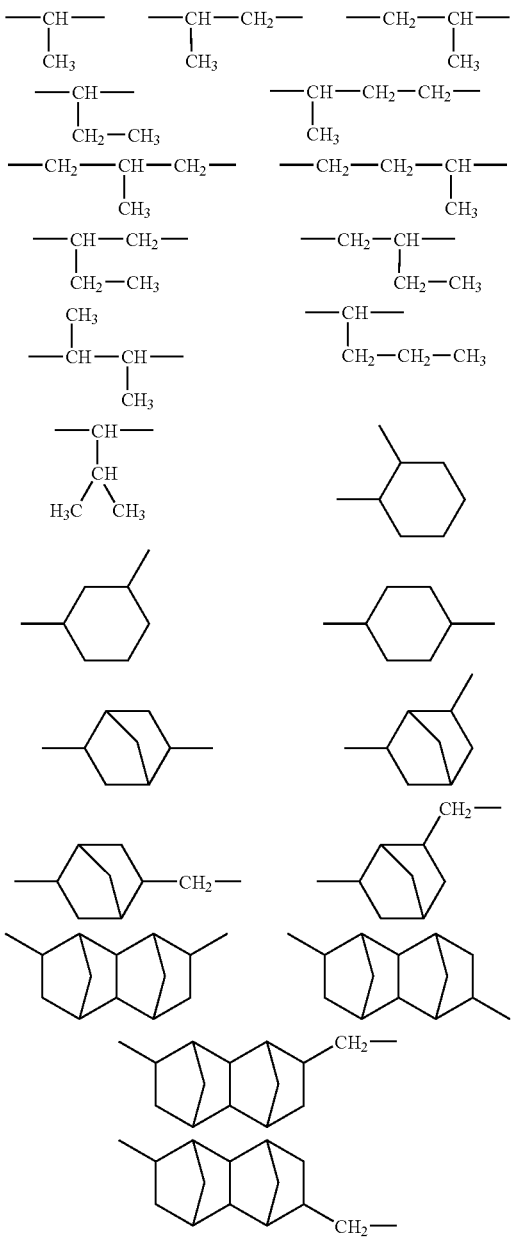

Therefore, the specific examples of the novel thiol compound of the present invention represented by the formula (1) include the following compounds, but the thiol compound of the present invention is not limited thereto.

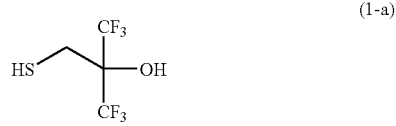
(1-a)

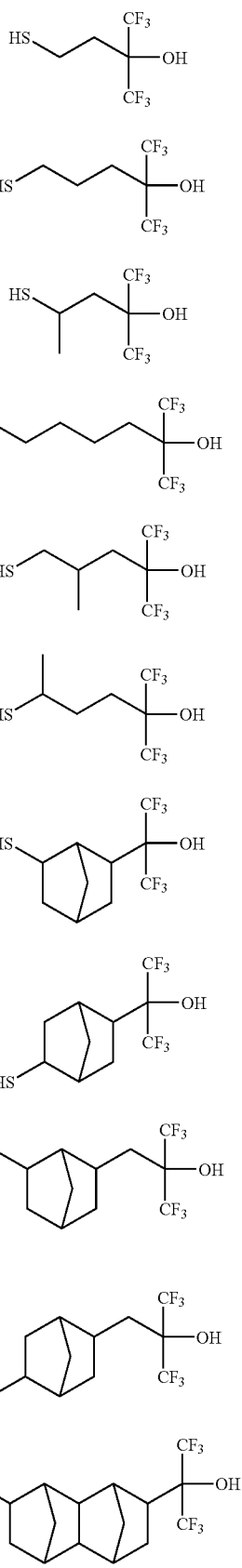

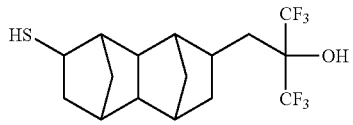

The method for producing the novel thiol compound of the present invention is not particularly limited, and the thiol compound can be readily synthesized by following methods. For example, addition of hydrogen sulfide to a compound comprising an ethylenic double bond and 2-hydroxy-1,1,1,3,3,3-hexafluoro-2-propyl group such as 4,4-bis (trifluoromethyl)-4-hydroxy-1-butene and 5-(2-hydroxy-1,1,1,3,3,3-hexafluoro-2-propyl) norbornene; addition of thiocarboxylic acid such as thioacetic acid and thiopropionic acid to the above compound having the ethylenic double bond followed by hydrolysis or alcoholysis; hydrolysis of thiuronium salt synthesized by the reaction of thiourea and the compound comprising 2-hydroxy-1,1,1,3,3,3-hexafluoro-2-propyl group and chlorine or bromine atoms such as 4-chloro-1,1-bis (trifluoro-methyl)-1-butanol; and the like can be used.

Also, the copolymer of the present invention is obtained by using the thiol compound represented by the formula (1) as the chain transfer agent in the radical copolymerization of two or more polymerizable compounds having an ethylenic double bond, and comprises the structure represented by the following formula (2):

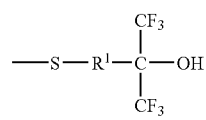

wherein $R^1$ is a bivalent substituent selected from linear, branched or cyclic saturated hydrocarbon having 1 to 15 carbon atoms, as the end group.

Due to extremely strong electron withdrawing of tri-trifluoromethyl group, the hydroxyl group comprised in the above terminal structure has a low pKa value compared to oridinal alcoholic hydroxyl groups and exhibits the pKa value equivalent to or less than those of phenolic hydroxyl groups. Thus, the copolymer of the present invention is excellent in adhesion to the substrate used for semiconductor lithography, and can be used suitably for film-coating lithograpy such as resist film and anti-reflective coating.

Furthermore, especially since this terminal structure has appropriate solubility to alkali developer equivalent to that of the phenolic hydroxyl group, it is anticipated that the resist pattern at an interface of an exposed part and an unexposed part is smoothened and line-edge roughness is improved. Here, the line-edge roughness means convexity and concavity in an edge of line pattern and substrate interface, and related to some resist film properties such as diffusion of acid generated from acid generator by the exposure and solubility of unexposed part in the alkali developer. The line-edge roughness declines a yield of semiconductor device due to deterioration of elective properties, and thus, especially a requirement of improve the line-edge roughness is getting strong along with the progress of microfabrication.

When the copolymer of the present invention is used for the semiconductor lithography, if the content of the end group represented by the formula (2) included in the copolymer is excessively low, the improving effects of adhesion to the substrate become insufficient. Therefore, the content of the end group represented by the formula (2) is preferably 0.1 mol % or more, and more preferably 0.5 mol % or more compared to a mole number of the monomer units in the copolymer.

To make the content of the end group represented by the formula (2) within the above range, it is prefer to make the amount of the thiol compound of the present invention to be used as the chain transfer agent to preferably 0.1 mol or more, and more preferably 0.5 mol or more based on 100 mol of the basic ingredient monomers. When the more amount of the chain transfer agent is used, the content of the above terminal structure included in the copolymer becomes higher, whereas a molecular weight of the resultant copolymer becomes smaller. Therefore the amount of the chain transfer is selected in the range where the copolymer having the desired molecular weight can be obtained.

The weight-average molecular weight (Mw) of the copolymer of the present invention is preferably in the range of 2,000 to 40,000, and more preferably in the range of 3,000 to 30,000. When it is excessively high, solubility of the copolymer into the solvent for coating or alkali developer becomes low. When it is excessively low, coating film performance becomes poor.

The monomers as the raw material of the copolymer of the present invention is not limited as long as they are polymerizable compounds having an ethylenic double bond. But however, when the resultant copolymer is used as the coating polymer in the semiconductor lithography, the structure is different depending on its usage.

First, when the resultant copolymer is used as the resist polymer, the copolymer of the present invention is comprising at least a repeating unit having a structure which is decomposed by an acid and becomes soluble in an alkali developer, more specifically, the repeating unit (A) having the structure where a non-polar substituent is eliminated by the acid and a polar group soluble in the alkali developer emerges, and a repeating unit (B) having a polar group to enhance adhesion to a substrate. And if necessary, the copolymer is comprising a repeating unit (C) having a non-polar and acid-stable substituent to regulate solubility in the resist solvent or the alkali developer.

The structure which is decomposed by the acid and becomes alkali-soluble in the repeating unit (A) means a conventional structure for resist polymer, and can be obtained by co-polymerization of the monomer having the structure which is decomposed by the acid and becomes alkali-soluble, or by copolymerization of the monomer having an alkali-soluble polar structure (alkali-soluble group) and followed by protection of the alkali-soluble group by an acid-labil non-polarstructure (acid-labil protecting group).

The monomer having the structure which is decomposed by the acid to become alkali-soluble can include compounds having alkali-soluble groups protected by acid-labil protecting groups, and for example, can include compounds having phenolic hydroxyl group, carboxyl group or hydroxylfluoroalkyl group protected by the acid-labil protecting groups.

Therefore, the polymerizable compounds having the alkali-soluble groups can include hydroxystyrenes such as p-hydroxystyrene, m-hydroxystyrene and p-hydroxy-α-methylstyrene; carboxylic acids having ethylenical double bonds such as acrylic acid, methacrylic acid, tri-fluoromethyl acrylic acid, 5-norbornene-2-carboxylic acid, 2-trifluoromethyl-5-norbornene-2-carboxylic acid and carboxytetracyclo [4.4.0.1$^{2,5}$.1$^{7,10}$] dodecylmethacrylate; polymerizable compounds having hydroxyfluoroalkyl groups such as p-(2-hydroxy-1,1,1,3,3,3-hexafluoro-2-propyl) styrene, 2-(4-(2-hydroxy-1,1,1,3,3,3-hexafluoro-2-propyl) cyclo-hexyl)-1,1,1,3,3,3-hexafluoropropyl acrylate, 2-(4-(2-hydroxy-1,1,1,3,3,3-hexafluoro-2-propyl) cyclo-hexyl)-1,1,1,3,3,3-hexafluoropropyl trifluoromethylacrylate and 5-(2-hydroxy-1,1,1,3,3,3-hexafluoro-2-propyl) methyl-2-norbornene, and the like.

The acid-labil protecting groups can include saturated hydrocarbon groups such as tert-butyl group, tert-amyl group, 1-methyl-1-cyclopentyl group, 1-ethyl-1-cyclopentyl group, 1-methyl-1-cyclohexyl group, 1-ethyl-1-cyclohexyl group, 2-methyl-2-adamantyl group, 2-ethyl-2-adamantyl group, 2-propyl-2-adamantyl group, 2-(1-adamantyl)-2-propyl group, 8-methyl-8-tricyclo [5.2.1.0$^{2,6}$.] decanyl group, 8-ethyl-8-tricyclo [5.2.1.0$^{2,6}$.] decanyl group, 8-methyl-8-tetracyclo [4.4.0.1$^{2,5}$.1$^{7,10}$] dodecanyl group and 8-ethyl-8-tetracyclo [4.4.0.1$^{2,5}$.1$^{7,10}$] dodecanyl group; oxygen-containing hydrocarbon groups such as 1-methoxyethyl group, 1-ethoxyethyl group, 1-isopropoxyethyl group, 1-n-butoxyethyl group, 1-tert-butoxyathyl group, 1-cyclopentyloxyethyl group, 1-cyclohexyloxyethyl group, 1-tricyclo [5.2.1.0$^{2,6}$] decanyloxyethyl group, methoxymethyl group, ethoxymethyl group, iso-propoxymethyl group, n-butoxymethyl group, tert-butoxymethyl group, cyclopentyloxymethyl group, cyclohexyloxymethyl group, tricyclo [5.2.1.0$^{2,6}$] decanyloxymethyl group and tert-butoxycarbonyl group; and the like.

In the case of the copolymerization of the monomer having the alkali-soluble group and followed by protection of the alkali-soluble group by the acid-labil group, the above compound having the alkali-soluble group can be used for the co-polymerization and the alkali-soluble group can be substituted to the acid-labil protecting group by subsequent reaction under an acid catalyst with the compound capable to give the substituent such as vinyl ethers and haloalkyl ethers which is not dissolved in alkali. The acid catalysts used for the reaction can include p-toluenesulfonic acid, trifluoroacetic acid, strongly acidic cation exchange resin and the like.

At the same time, the monomers which give the repeating unit (B) having the polar group to enhance the adhesion to the substrate can include, for example, compounds having phenolic hydroxyl groups, carboxyl groups and hydroxyfluoroalkyl groups as the polar groups, and specifically can include, for example, hydroxystyrenes and carboxylic acids having an ethylenic double bond described above as the polymerizable compounds having the alkali-soluble groups, the polymerizable compounds having hydroxyfluoroalkyl groups, and monomers where polar groups are further substituted thereto, and additionally monomers where the polar groups are bound to an alicyclic structure such as norbornene ring and tetracyclododecene ring.

As the above polar group introduced in the repeating unit (B), particularly preferable are the substituents comprising a lactone structure, and for example, it is possible to include substituents comprising the lactone structure such as γ-butyrolactone, γ-valerolactone, δ-valerolactone, 1,3-cyclohexanecarbolactone, 2,6-norbornanecarbolactone, 4-oxatricyclo [5.2.1.0$^{2,6}$] decane-3-one and mevalonic acid δ-lactone. Besides, the polar groups other than the lactone structure can include hydroxyalkyl groups such as hydroxymethyl group, hydroxyethyl group, hydroxypropyl group and 3-hydroxy-1-adamantyl group, and the like Further the monomers comprising the repeating unit (C) having non-polar acid-stable substituents to regulate solubility in the resist solvent or the alkali developer can include, for example, compounds having substituted or unsubstituted alkyl or aryl groups containing no polar group, and polar groups protected with non-polar and acid-stable groups, and specifically can include, for example, styrenes such as styrene, α-stylene and p-methylstyrene; ester compounds where acid stable non-polar groups are substituted to carboxylic acid having an ethylenic double bond such as acrylic acid, methacrylic acid, trifluoromethylacrylic acid, norbornenecarboxylic acid, 2-trifluoromethylnorbornenecarboxylic acid and carboxytetracyclo [$4.4.0.1^{2,5}.1^{7,10}$] dodecyl methacrylate; alicyclic hydrocarbon compounds having an ethylenic double bond such as norbornene and tetracyclododecene, and the like. Examples of acid-stable non-polar substituents, which are substituted to the above carboxylic acid and give ester compounds, can include methyl group, ethyl group, cyclopentyl group, cyclohexyl group, isobornyl group, tricyclo [$5.2.1.0^{2,6}$] decanyl group, 2-adamantyl group, tetracyclo [$4.4.0.1^{2,5}.1^{7,10}$] dodecyl group and the like.

These monomers can be used in mixture with one or two or more types for the respective repeating units (A), (B) and (C), and a composition ratio of the respective repeating units in the obtained resist polymer can be selected within the range in which the performance of resist is not impaired. The composition ratio of the repeating unit (A) is preferably from 10 to 70 mol %, and more preferably from 10 to 60 mol %. And, the composition ratio of the repeating unit (B) is preferably from 30 to 90 mol %, and more preferably from 40 to 90 mol %, but if some monomer units have the same polar group, it is preferably 70 mol % or less. Moreover, the composition ratio of the repeating unit (C) is preferably from 0 to 50 mol %, and more preferably, from 0 to 40 mol %.

Besides, when the copolymer of the present invention is used as a bottom coating polymer in the multi-layer resist application or an anti-reflective coating polymer in the multi-layer resist application, the copolymer has the structure where the above repeating unit (A) which is decomposed by the acid and becomes alkali-soluble is eliminated from the structure of the resist polymer. The composition ratio of the respective repeating units in the copolymer cannot be completely defined because it is different depending on the intended use of coating films, but generally, the composition ratio of the repeating unit (B) is selected in the range of 10 to 100 mol %, and the composition ratio of the repeating unit (C) is selected in the range of 0 to 90 mol %.

When the copolymer of the present invention is used as the anti-reflective coating polymer, it is required to comprise a crosslinking point and a structure which absorbs radiation irradiated in the lithography. The crosslinking points include reactive substituents which can give ester linkages or urethane linkages such as hydroxyl group, amino group and epoxy group. As the monomer containing the reactive substituent as the crosslinking point, it is possible to appropriately use hydroxy styrenes such as p-hydroxystyrene and m-hydroxystyrene. Moreover, any substituted monomers exemplified above can be used as long as they have the reactive substituents such as hydroxy group, amino group and epoxy group.

The above structure which absorbs the radiation is different depending on wavelength of the light source. For example, the structures comprising benzene ring and the derivatives are used suitably for the ArF excimer laser. The monomers comprising such a radiation absorbing structure can include styrenes such as styrene, α-methylstyrene, p-methylstyrene, p-hydroxystyrene and m-hydroxystyrene; esters having an aromatic nucleus and an ethylenic double bond such as substituted or unsubstituted phenyl (meth) acrylate, substituted or unsubstituted naphthalene (meth) acrylate and substituted or unsubstituted anthracenemethyl (meth)acrylate, and the like. The monomer having the radiation absorbing structure may be used as either the above repeating unit (B) or (C) depending on the presence or absence of the polar group. It is preferred that the composition ratio of the monomer having the radiation absorbing structure is selected in the range of 10 to 100 mol %.

The polymerization initiator which can be used in the polymerization for producing the copolymer of the present invention include, but are not limited to, for example, azo compounds such as 2,2'-azobisisobutyronitrile, 2,2'-azobis (2-methylbutyronitrile), dimethyl 2,2'-azobis (isobutylate), 1,1'-azobis (cyclohexane-1-carbonitrile) and 4,4'-azobis (4-cyanovaleric acid), and organic peroxide compounds such as didecanoyl peroxide, dilauroyl peroxide, dibenzoyl peroxide, bis (3,5,5-trimethylhexanoyl) peroxide, succinic acid peroxide and tert-butyl peroxy-2-ethylhexanoate. The polymerization initiator may be used either individually or in combination of two or more. The amount of the polymerization initiator used in the present invention is not determinable completely, because it is depending on types and amounts of monomers and chain transfer agents, and polymerization conditions like polymerization temperature and polymerization solvents. Typically, the amount of the initiator is selected from the range of 0.01 to 10 mol and preferably from 0.1 to 5 mol based on 1 mol of the chain transfer agent.

As the polymerization method to produce the copolymer of the present invention, solution polymerization is preferable, and it is preferable that the radical copolymerization is carried out in a polymerization solvent containing the monomers, the polymerization initiator and the chain transfer agent. The solution polymerization may be performed by a so-called batch polymerization method where all of the monomers, the initiator and the chain transfer agent charged into the polymerization solvent at once and heated to polymerization temperature, or a so-called dropping polymerization method where the solution containing parts or all of the monomers, initiator and chain transfer agent are continuously dropped into polymerization system heated to the polymerization temperature.

The polymerization solvents are not particularly limited as long as they are the solvents which allow the monomers, the resultant copolymer, the polymerization initiator and the chain transfer agent to be dissolved. Specific examples of the polymerization solvents can include ketones such as acetone, methyl ethyl ketone and methyl amyl ketone; ethers such as tetrahydrofuran, dioxane, glyme and propylene glycol monomethyl ether; esters such as ethyl acetate and ethyl lactate; etheresters such as propylene glycol methyl ether acetate; lactones such as γ-butyrolactone, and the like, and these can be used alone or in mixture. The amount of the polymerization solvent to be used is not particularly limited, but is typically from 0.5 to 20 weight parts, and preferably from 1 to 10 weight parts based on 1 weight part of the monomers. When the amount of the solvent is excessively small, the monomer or the copolymer precipitates in some cases. When it is excessively high, velocity of the polymerization reaction becomes insufficient in some cases.

The reaction condition of polymerization is not particularly limited, but generally, the reaction temperature is preferably from about 60° C. to 100° C., and the reaction time is preferably from about one hour to 20 hours.

The copolymer after the copolymerization can be purified by adding the polymer solution to a poor solvent, or a mixed solvent of the poor solvent and a good solvent dropwise to precipitate, and further washing with above solvent if necessary for removing unwanted substances such as residual monomers, oligomers, the polymerization initiator, the chain transfer agent and reaction residues thereof. The poor solvent is not particularly limited as long as it is the solvent in which the resultant copolymer is not dissolved, and for example, it is possible to use water, alcohols such as methanol and isopropanol, saturated hydrocarbons such as hexane and heptane, and the like. The good solvent is not particularly limited as long as it is the solvent in which the monomers, the oligomers, the polymerization initiator, the chain transfer agent and the reaction residues thereof are dissolved, but it is preferred that the good solvent is the same as the polymerization solvent in terms of management of production steps.

Types of usage of the copolymer of the present invention obtained as the above are not particularly limited. When used as the film-coating polymer in the semiconductor lithography, typically the copolymer is used by dissolving in the coating solvent. Because the copolymer after the purification has the solvent used at the purification, it is possible to complete a coating solution by vacuum drying followed by dissolving in a solvent used for the film-coating, or once dissolving in the solvent used for the film-coating or the good solvent such as the polymerization solvent and subsequently distilling off the other solvents in vacuum with supplying the solvent used for the film-coating if necessary.

The above solvent used for the film-coating is not particularly limited as long as it is the solvent dissolving the copolymer, but is typically selected by taking a boiling point, effects on the semiconductor substrate and the other coating films and absorption of radiation used for the lithography into consideration. Examples of the solvents generally used for the film-coating include solvents such as propylene glycol methyl ether acetate, ethyl lactate, methyl amyl ketone, γ-butyrolactone and cyclohexane. The amount of the solvent to be used is not particularly limited, but is typically in the range of 1 to 20 weight parts based on 1 weight part of the copolymer.

When the copolymer of the present invention is used as the resist polymer, it is possible to complete a resist composition by blending in this coating solution a photoacid generator, and an acid diffusion control agent such as a nitrogen-containing basic compound capable of suppressing the rate of acid diffusion with in parts which are not exposed. As the photoacid generator, it is possible to use those generally used as basic ingredients for resist such as onium salts, sulfone compounds, sulfonate esters, sulfonimide compounds and di-sulfonyldiazomethane compounds. Also, in the resist composition, it is possible to blend other compounds commonly used as additives for resist such as a dissolution inhibitor, a sensitizer and dyes.

The combination ratio of respective ingredients (excluding the resist solvent) in the resist composition is not particularly limited, but is generally selected from the ranges of 10 to 50% by mass of polymer concentration, 0.1 to 10% by mass of photoacid generator and 0.001 to 10% by mass of acid diffusion control agent.

Also, when the obtained copolymer of the present invention is used as the anti-reflective coating, the copolymer is used alone or in mixture with bifunctional or more isocyanate, amine, epoxide and the like capable of crosslinking with the polymers.

EXAMPLES

Next, the present invention is further described by following examples, but the invention is not limited to these examples. The average copolymer composition of the obtained copolymer was calculated by a result of $^{13}$C-NMR measurement. The weight average molecular weight Mw and the dispersion Mw/Mn were calculated by the measurement result of gel permeation chromatography (GPC).

Example 1

Production of 4-mercapto-1,1-bis (trifluoromethyl)-1-butanol

Under a nitrogen atmosphere, 20 g of 4,4-bis (trifluoromethyl)-4-hydroxy-1-butene (96.1 mmol), 8.05 g of thioacetic acid (105.7 mmol), 60 g of 1,4-dioxane and 0.79 g of 2,2'-azobisisobutyronitrile (hereinafter abbreviated as AIBN) (4.8 mmol) were put into a flask equipped with a stirring bar, a thermometer and a condenser, and heated with stirring. During the reaction, thioacetic acid and AIBN were appropriately added and after confirming that a substrate was completely consumed, the reaction solution was distilled as it was under reduced pressure to yield an intermediate product, 22 g of 4-acetylthio-1,1-bis (trifluoromethyl)-1-butanol (76.9 mmol).

Then, under the nitrogen atmosphere, 14 g of 4-acetylthio-1,1-bis (trifluoromethyl)-1-butanol (49.3 mmol) obtained above, 12.6 g of methanol and 2.81 g of para-toluenesulfonate hydrate (30 mol %) were put into a flask equipped with a stirring bar, a thermometer and a condenser, and stirred with reflux until the substrate was completely consumed. Subsequently, the reaction solution was cooled to room temperature, extracted with ethyl acetate followed by being washed, and then distilled under reduced pressure to yield 10.7 g of 4-mercapto-1,1-bis (trifluoromethyl)-1-butanol represented by the following formula (1-c) (44.3 mmol).

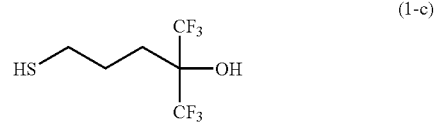

(1-c)

The structure of the obtained compound (1-c) was confirmed by the following results of analysis.

(1) Mass Spectrum (GC-MS) m/z: 242 (M$^+$), 209, 190, 171, 155, 139, 121, 91, 69, 47 (2) $^1$H-NMR spectrum (CDCl$_3$ solvent) δ(ppm):3.48(1H, br), 2.58(2H, q like, J=5.4 Hz, 7.8), 2.10 to 2.05(2H, m), 1.92 to 1.85(2H, m), 1.43(1H, t, J=7.8 Hz) (3) $^{13}$C-NMR spectrum (CDCl$_3$ solvent) δ(ppm): 123.1(CF$_3$, q, J=287 Hz), 77.4 to 75.4(C—CF$_3$,m), 28.9 (CH$_2$), 26.1(CH$_2$), 24.5(CH$_2$)

Example 2

Production of copolymer 1 represented by the following structural formula and containing —SC$_3$H$_6$C(CF$_3$)$_2$OH group as the end group:

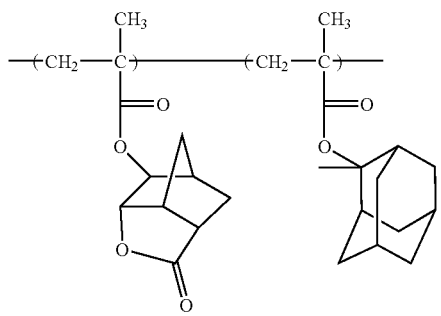

In a container retained at the nitrogen atmosphere, 150 g of methyl ethyl ketone (hereinafter, abbreviated as MEK), 33.2 g of 5-methacryloyloxy-2,6-norbornanecarbolactone (hereinafter, abbreviated as NLM), 44.7 g of 2-methyl-2-adamantyl methacrylate (hereinafter, abbreviated as MAM) and 1.65 g of the compound (1-c) obtained in the example 1 as a chain transfer agent were placed and dissolved to prepare a monomer feed solution. Also, in another container retained at the nitrogen atmosphere, 20 g of MEK and 0.45 g of AIBN as a polymerization initiator were placed and dissolved to prepare an initiator feed solution. In a polymerization chamber retained at the nitrogen atmosphere, 65 g of MEK was placed and warmed to 80° C. with stirring, and subsequently, the monomer feed solution and the initiator feed solution were fed into the polymerization chamber retained at 80° C. over 4 hours to polymerize. Feed ratios of the basic ingredient monomers and the chain transfer agent were shown in Table 1. After the completion of feeding, the reaction was matured for two hours with retaining at 80° C. After polymerization, the polymer solution was cooled to the room temperature and added into methanol dropwise to precipitate. The precipitate was filtrated and washed with methanol. Then the resultant wet cake was dried in a vacuum dryer to yield white polymer powder (copolymer 1). When the content of the terminal structure derived from the thiol compound in the obtained polymer was calculated by $^{13}$C-NMR measurement, it was 1.5 mol % based on the total number of monomer units contained in the polymer.

Besides, the obtained copolymer 1 was dissolved in propylene glycol methyl ether acetate (hereinafter abbreviated as PGMEA) to make a 20% solution, which was then spin-coated onto a silicon wafer precedently treated with 1,1,1,3,3,3-hexamethyldisilazane, and baked at 110° C. for 90 seconds to form a coating film with film thickness of 1.0 μm. For the obtained coating films, a peel strength and a peel mode of the coating film were measured at a constant load mode using SAICAS CN-20 supplied from Daipla Wintes. Measurement results of physical properties and the peel strength/peel mode of the obtained copolymer 1 were shown in Table 2.

Example 3

Production of copolymer 2 represented by the following structural formula and containing —SC$_3$H$_6$C(CF$_3$)$_2$OH group as the end group:

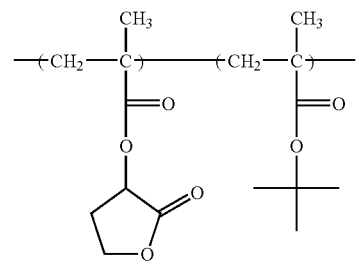

In a container retained at the nitrogen atmosphere, 150 g of MEK, 28.9 g of γ-butyrolactone-2-yl methacrylate (hereinafter abbreviated as GBLM), 24.2 g of tert-butyl methacrylate (hereinafter abbreviated as TBMA) and 1.65 g of the compound (1-c) obtained in the example 1 as a chain transfer agent were placed and dissolved to prepare a monomer feed solution. Also, in another container retained at the nitrogen atmosphere, 20 g of MEK and 1.5 g of AIBN as a polymerization initiator were placed and dissolved to prepare an initiator feed solution. In a polymerization chamber retained at the nitrogen atmosphere, 65 g of MEK was placed and warmed to 80° C. with stirring, and subsequently, the monomer feed solution and the initiator feed solution were fed into the polymerization chamber retained at 80° C. over 4 hours to polymerize. Feed ratios of the basic ingredient monomers and the chain transfer agent were shown in Table 1. After the completion of feeding, there action was matured for two hours with retaining at 80° C. After the polymerization, the polymer solution was cooled to the room temperature and added into methanol dropwise to precipitate. The precipitate was filtrated and washed with methanol. Then the resultant wet cake was dried in a vacuum dryer to yield white polymer powder (copolymer 2). When the content of the terminal structure derived from the thiol compound in the obtained polymer was calculated by $^{13}$C-NMR measurement, it was 1.5 mol % based on the total number of monomer units contained in the polymer. Characteristics of the copolymer 2 and the peel strength and the peel mode of the coating film obtained as is the case with the example 1 were shown in Table 2.

Comparative Example 1

The comparative example 1 was made by the same procedure as the example 2, except using 0.53 g of 2-mercaptoethanol (hereinafter abbreviated as MEO) as the chain transfer agent in the example 2. When the content of the terminal structure derived from MEO in the obtained polymer was calculated by $^{13}$C-NMR measurement, it was 1.5 mol % based on the total number of monomer units contained in the polymer. Feed ratios of monomers and the chain transfer agent were shown in Table 1. Characteristics of the copolymer 3 and the peel strength and the peel mode of the coating film were shown in Table 2.

Comparative Example 2

The comparative example 2 was made by the same procedure as the example 3 except using 0.53 g of MEO as the chain transfer agent. When the content of the terminal structure derived from MEO in the obtained polymer was calculated by $^{13}$C-NMR measurement, it was 1.5 mol % based on the total number of monomer units contained in the polymer. Feed ratios of monomers and the chain transfer agent were shown in Table 1, and characteristics of the copolymer 4 and the peel strength and the peel mode of the coating film were shown in Table 2.

Example 4

Production of 1,1,1,3,3,3-hexafluoro-2-(5- or 6-mercapto-bicyclo[2.2.1]hepto-2-ylmethyl)propan-2-ol 12.21 g (160 mmol) of thioacetic acid was put into a three-necked flask equipped with a stirring bar, a thermometer and a condenser, and heated to 80° C. After the internal temperature of said flask reached to 80° C., mixed solution containing 0.336 g (1.46 mmol) of di-methyl-2,2'-azobisiosbutyrate and 40 g (146 mmol) of 2-bicyclo[2.2.1]hepto-5-en-2-ylmethyl-1,1,1,3,3,3-hexafluoropropan-2-ol was added from a dropping funnel for 2 hours, followed by stirring at 80° C. for 2 hours. 19 g of methanol and 3.384 g (17.8 mmol) of para-toluenesulfonic acid monohydrate was added and stirred was conducted under reflux for 2 hours. Then, the reaction mixture was cooled to room temperature, and washed by 7% aqueous by 7% aqueous solution of sodium bicarbonate and water each 2 times. Thus obtained organic layer was distilled under reduced pressure to obtain 24.7 g of the titled novel thiol compound, 1,1,1,3,3,3-hexafluoro-2-(5- or 6-mercapto-bicyclo[2.2.1]hepto-2-ylmethyl)propan-2-ol. The titled compound was a mixture of 1,1,1,3,3,3-hexafluoro-2-(6-mercapto-bicyclo[2.2.1]hepto-2-ylmethyl)propan-2-ol represented by the following formula (1-j) and 1,1,1,3,3,3-hexafluoro-2-(6-mercapto-bicyclo[2.2.1]hepto-2-ylmethyl)propan-2-ol represented by the following formula (1-k), and this compound is referred to as compound (1-jk).

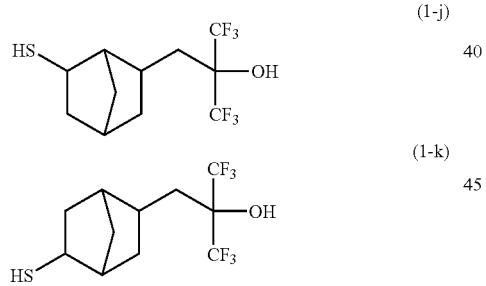

(1-j)

(1-k)

The structure of the obtained compound (1-jk) was confirmed that 4 isomers represented by following formula were contained, by the following results of analysis. The purity measured by gas chromatography was 98% (total of 4 isomers).

(1) Mass spectrum (GC-MS) m/z: 308 (M$^+$) (2) $^1$H-NMR spectrum (DMSO-d$_6$ solvent) δ(ppm):7.65 to 7.58(1H,br), 3.14 to 2.78(1H,m),2.54 to 2.48(1H, m, S$\underline{H}$), 2.17 to 1.12 (10H, m), 0.08 to 0.66(1H, m) (3) $^{13}$C-NMR spectrum (C$_6$D$_6$ solvent) δ(ppm): 128.2(q, CF$_3$), 76.9(m, $\underline{C}$—CF$_3$), 53.3 (CH), 51.9(CH), 47.5(CH), 47.2(CH), 43.5(CH), 43.0(CH$_2$), 42.5(CH), 42.4(CH$_2$), 41.1(CH$_2$), 40.5(CH), 40.3(CH), 39.5 (CH), 38.8(CH$_2$), 38.4(CH$_2$), 37.9(CH), 37.6(CH$_2$), 37.3 (CH), 36.9(CH$_2$), 36.7(CH$_2$), 36.6(CH$_2$), 36.4(CH$_2$), 35.5 (CH), 35.3(CH$_2$), 34.8(CH), 34.0(CH)),33.9(CH), 33.0(CH$_2$), 32.5(CH$_2$), 32.4(CH), 32.3(CH$_2$), 32.1(CH$_2$)

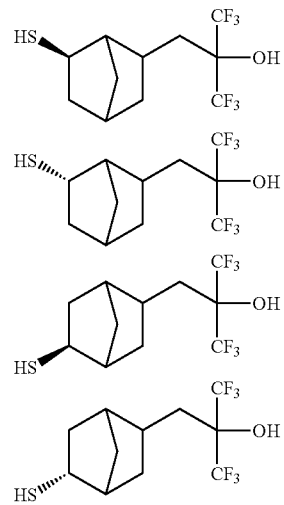

Example 5

Production of copolymer 5 represented by the following structural formula and containing the partial end group represented by the following formula and derived from the thiol compound represented by the following formula (3):

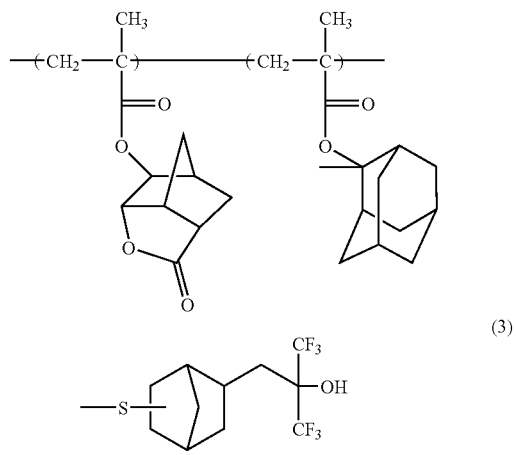

(3)

The example 5 was made by the same procedure as the example 2, except using 2.10 g of the compound (1-jk) obtained in Example 4 as the chain transfer agent. When the content of the terminal structure derived from the thiol compound in the obtained polymer was calculated by $^{13}$C-NMR measurement, it was 1.4 mol % based on the total number of monomer units contained in the polymer. Feed ratios of monomers and the chain transfer agent were shown in Table 1. Characteristics of the copolymer 5 and the peel strength and the peel mode of the coating film were shown in Table 2.

Example 6

Production of copolymer 6 represented by the following structural formula and containing the partial end group represented by the following formula and derived from the thiol compound represented by the following formula (3):

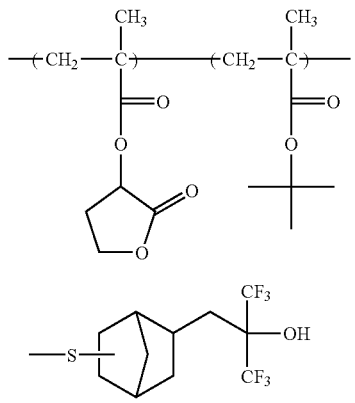

(3)

The example 6 was made by the same procedure as the example 3, except using 2.10 g of the compound (1-jk) obtained in Example 4 as the chain transfer agent. When the content of the terminal structure derived from the thiol compound in the obtained polymer was calculated by $^{13}$C-NMR measurement, it was 1.4 mol % based on the total number of monomer units contained in the polymer. Feed ratios of monomers and the chain transfer agent were shown in Table 1. Characteristics of the copolymer 6 and the peel strength and the peel mode of the coating film were shown in Table 2.

TABLE 1

| | Chain transfer Agent Feed Amount (mol %) | | Monomer Feed Ratio (mol %) | | | | |
|---|---|---|---|---|---|---|---|
| | (1-C) | (1-jk) | MEO | NLM | MAM | GBLM | TBMA |
| Example 2 | 2.0 | — | — | 44 | 56 | — | — |
| Example 3 | 2.0 | — | — | — | — | 50 | 50 |
| Example 5 | — | 2.0 | — | 44 | 56 | — | — |
| Example 6 | — | 2.0 | — | — | — | 50 | 50 |
| Comparative example 1 | — | — | 2.0 | 44 | 56 | — | — |
| Comparative example 2 | — | — | 2.0 | — | — | 50 | 50 | peel strength compared to the prior art and is extremely excellent in adhesion to the substrate.

ADVANTAGE OF THE INVENTION

The thiol compound of the present invention is useful as a chain transfer agent for producing the coating polymers excellent in adhesion to the substrate in semiconductor lithography. The copolymer of the present invention obtained by the use thereof as the chain transfer agent is excellent in adhesion to the substrate, and can be used suitably as the polymer for the coating film having durability against pattern collapse in the finer pattern formation. In addition, in the copolymer of the present invention, since the end group of polymer derived from the thiol compound of the present invention exhibits moderate alkali solubility, the resist pattern at the interface of the exposed part and the unexposed part is smoothened at the pattern formation, and improving effects of line edge roughness are anticipated.

What is claimed is:

1. A copolymer obtained by using a thiol compound represented by the formula (1);

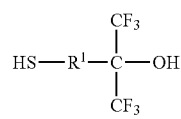

(1)

(wherein $R^1$ is a bivalent substituent selected from linear, branched or cyclic saturated hydrocarbon having 1 to 15 carbon atoms.) as a chain transfer agent, in polymerization of two or more polymerizable compounds having an ethylenic double bond.

2. The copolymer according to claim 1 comprising a structure represented by the formula (2);

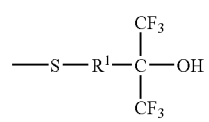

(2)

TABLE 2

| | Chain Transfer Agent Content (mol %) | | Average Composition of Copolymer (mol %) | | | | | GPC | | Peel Strength (kN/m) | Peel Mode |
|---|---|---|---|---|---|---|---|---|---|---|---|
| | (3-C) | (1-jk) | MEO | NLM | MAM | GBLM | TBMA | Mw | Mw/Mn | | |
| Example 2 | 1.5 | — | — | 47 | 53 | — | — | 9,300 | 1.57 | 0.183 | * |
| Example 3 | 1.5 | — | — | — | — | 54 | 46 | 8,100 | 1.53 | 0.185 | * |
| Example 5 | — | 1.4 | — | 47 | 53 | — | — | 9,500 | 1.60 | 0.179 | * |
| Example 6 | — | 1.4 | — | — | — | 54 | 46 | 8,200 | 1.53 | 0.180 | * |
| Comparative Example 1 | — | — | 1.7 | 47 | 53 | — | — | 9,000 | 1.60 | 0.102 | * |
| Comparative Example 2 | — | — | 1.7 | — | — | 54 | 46 | 7,900 | 1.55 | 0.101 | * |

* Interfacial failure

As is shown in these results, it is found that the copolymer obtained by using the thiol compound of the present invention as the chain transfer agent is remarkably improved in (wherein $R^1$ is a bivalent substituent selected from linear, branched or cyclic saturated hydrocarbon having 1 to 15 carbon atoms.) as the end group.

3. The copolymer according to claim 1 used as a coating polymer in semiconductor lithography.

4. The copolymer according to claim 3, which has at least a repeating unit having a structure which is decomposed by an acid to become soluble in an alkali developer and a repeating unit having a polar group to enhance adhesion to a substrate, and which is used as a resist polymer.

5. The copolymer according to claim 3 which is used as an anti-reflective coating polymer coated under the resist film.

* * * * *